US00PP09393P

United States Patent [19]

Bridgen

[11] Patent Number: Plant 9,393

[45] Date of Patent: Dec. 5, 1995

[54] ALSTROEMERIA 'FREEDOM'

[75] Inventor: Mark P. Bridgen, Storrs, Conn.

[73] Assignee: University of Connecticut, Storrs, Conn.

[21] Appl. No.: 355,045

[22] Filed: Dec. 13, 1994

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Hamilton, Brook, Smith, Reynolds

[57] ABSTRACT

A new and distinct cultivar of Alstroemeria named 'Freedom' is characterized by blossoms that have tepals that are coral pink, tipped with green. There are short, thin dark maroon markings along the perimeter of the outer tepals. The inside circle of 3 tepals are the same color at their tips, but they are primarily white with narrow, longitudinal dark maroon/brown streaks; the top two tepals of this inner group of three also have pale yellow on their central portions. The individual florets are produced on short peduncles. The plant is also distinguished by its short (approximately 45 cm. when grown in full sun), but strong, stems and its upright and vigorous growth habit. There is a continuous production of flowers on its umbel arrangement of branches during each of its blooming seasons.

1 Drawing Sheet

SUMMARY OF THE INVENTION

This new and distinct cultivar of the botanical genus Alstroemeria (Lily-of-the-Incas, Inca Lily, or Peruvian Lily) is a product of my breeding program at the University of Connecticut in Storrs, Conn. The primary objective of my breeding program was the creation of new Alstroemeria cultivars for pot production and garden cultivation. This Alstroemeria plant originated as a seedling, designated as AC×RW, resulted from my crossing of plants selected from individually identified members of my breeding stock.

This plant was selected for propagation and is distinguishable from all other Alstroemeria varieties because it combines distinctive flower coloration and shape with a short growth habit and strong, upright flower stems. Numerous florets are produced on each flower stem. Asexual propagation of this new plant by root division was carried on under my direction at the University of Connecticut; successive generations of this plant have demonstrated that the distinctive characteristics of the parent hybrid hold true from generation to generation and appear to be firmly fixed. Micropropagation and traditional asexual propagation by rhizome division of this new cultivar is now being carried on at the University of Connecticut.

This cultivar has been observed in the greenhouse and in the field for several years but has not been observed under all possible environmental conditions. The phenotype may vary with variations in environment such as light intensity, temperature, nutrition and daylength.

BRIEF DESCRIPTION OF THE DRAWING

This new cultivar of Alstroemeria plant is illustrated by the accompanying photographic drawing in full color showing an umbel of the plant with open flowers. The color renditions are believed to be as close to the specific colors as is possible to obtain by conventional photographic procedures.

DETAILED DESCRIPTION OF THE NEW PLANT

The following is a detailed description of my new Alstroemeria plant with color designations according to the R.H.S.

Colour Chart of The Royal Horticultural Society of London, England. Colors were confirmed with CIELAB coordinates that were measured with a Minolta CR-200b Color Meter (Minolta, Ramsey, N.J.). The following observations, measurements, and comparisons describe plants grown in Storrs, Conn. under field conditions in full sun.

The Plant

Origin: Seedling.

Parentage:

*Seed parent.*—*Alstroemeria caryophyllaea.*

*Pollen parent.*—Breeding Stock Plant No. GP24 (unpatented).

Classification:

*Botanic.*—Alstroemeria hybrid L.

*Commercial.*—Alstroemeria; Lily-of-the-Incas; Inca Lily; Peruvian Lily.

Form: Herbaceous plant arising from an underground rhizome and having short, stout flowering stalks with flower-bearing branches of simple umbel form at its top.

Height: Approximately 45 cm.

Growth: Strong and upright.

Root stock: Tuberous.

Foliage:

*Quantity.*—Many.

*Number of leaves.*—Average of 33 per vegetative stem. Average of 21 per inflorescence stem.

*Size of leaf.*—Length: 11 cm. Diameter at widest point: 2.8 cm.

*Leaf shape.*—Simple, linear, resupinate leaves with parallel venation that are arranged alternatively; the shape of the leaves is elliptic with extended bases and broadly acuminate apices; leaf margins are entire.

*Texture.*—Glabrous leaf surfaces.

*Color.*—Green on both upper and under sides.

*Vegetative stem length.*—45 cm.

Rhizomes:

*Color.*—White.

The Bud

Form: Pear shaped becoming long and more pointed just before opening.

Size:

*Diameter.*—Approximately 1 cm. as the bud begins to form external pigments.

*Length.*—Approximately 3 cm. as the bud begins to form external pigments.

Calyx: The flower bud of this plant has not separate calyx and corolla; the six tepals of the flower are a perianth and divide simultaneously.

Opening rate: Normal.

Peduncle:

*Length.*—4.8 cm.

*Color.*—Green turning pinkish as it reaches anthesis.

The Flower

Blooming habit: Continuous and profuse after flower initiation.

Flower size: Large.

*Diameter.*—Approximately 4.0–5.0 cm.

*Depth.*—Approximately 5.0 cm.

Number of florets/inflorescence: Average 7.

Borne: Singly.

Shape: Flowers are zygmorphic, protandrous, and epigynous with inferior ovaries; flowers arise in a terminal bracted umbel of cymes. Mature blooms are funnel-shaped with tepal tips curling outward.

Inflorescence length: 45 cm.

Petalage:

*Number of petals.*—Six tepals.

*Arrangement.*—Two concentric circles of three tepals each.

*Form.*—The 3 outer tepals are spatulate with emarginate to mucronate apices that pinch together. The extreme 1–2 mm tip is greenish. The 3 inner tepals are also spatulate but are more narrow than the 3 outer tepals and have apiculate apices.

*Texture.*—Leathery.

*Appearance.*—Shiny.

*Color of petals.*—Outer tepals — Coral pink 52 A-B (fading to 54 A-B as the flower ages) with a gradation of color to white 155D at the base. There are short, narrow dark maroon 53A streaks at the edges of the tepals. Each tepal's extreme apex is light green 137D. Inner tepals — The bottom ⅔ to ¾ of the inner tepals are white 155D while the top portions are coral pink 52 A-B. There are numerous well-defined longitudinal dark maroon 53A streaks throughout. The two upper tepals of the central ring of 3 have a slight tinge of yellow 14C.

Peduncle:

*Length.*—4.8 cm.

*Color.*—Light green.

Persistence: The tepals fall off at senescence.

Lasting quality:

*On plant.*—Approximately 20–28 days.

*As a cut flower.*—Approximately 10–14 days.

Main stem of stalk:

*Length.*—45 cm.

*Character.*—Strong and upright.

*Number of leaves.*—Average of 21 per inflorescence stem.

*Size of leaf.*—Length: 10.5 cm. Diameter at widest point: 2.1 cm.

Reproductive Organs

Stamens:

*Number.*—Six.

*Arrangement.*—One opposite each petal.

Anthers:

*Size.*—6–8 mm.

*Color.*—Brownish gray.

Filaments:

*Length.*—Approximately 4 cm.

*Color.*—Pink.

Pistils:

*Number.*—One.

*Length.*—Approximately 4–4.5 cm.

*Color.*—Pink at the tip fading to white near the ovary.

Stigma:

*Color.*—Pink.

Fruit

Fertility: Sterile triploid (2n=3×=24).

Shape: Capsular.

Color at maturity: Light green with a reddish purple tinge.

This cultivar of Alstroemeria is characterized by its short growth habit and the distinctive coloration and shape, and short peduncles of its flowers which do not closely resemble that of any other Alstroemeria plant previously known to me. The large blossoms of this cultivar have tepals that are coral pink, tipped with green. There are short, thin dark maroon markings along the perimeter of the outer tepals. The inside circle of 3 tepals are the same color at their tips, but they are primarily white with narrow, longitudinal dark maroon/brown streaks; the top two tepals of this inner group of three also have pale yellow on their central portions. The individual florets are produced on short peduncles. The plant is also distinguished by its short (approximately 45 cm. when grown in full sun), but strong, stems and its upright and vigorous growth habit. There is a continuous production of flowers on its umbel arrangement of branches during each of its blooming seasons.

I claim:

1. A new and distinctive Alstroemeria plant substantially as shown and described, distinguished by its unique flower color and shape, short growth habit, strong and numerous flowering stems, and numerous florets per inflorescence.

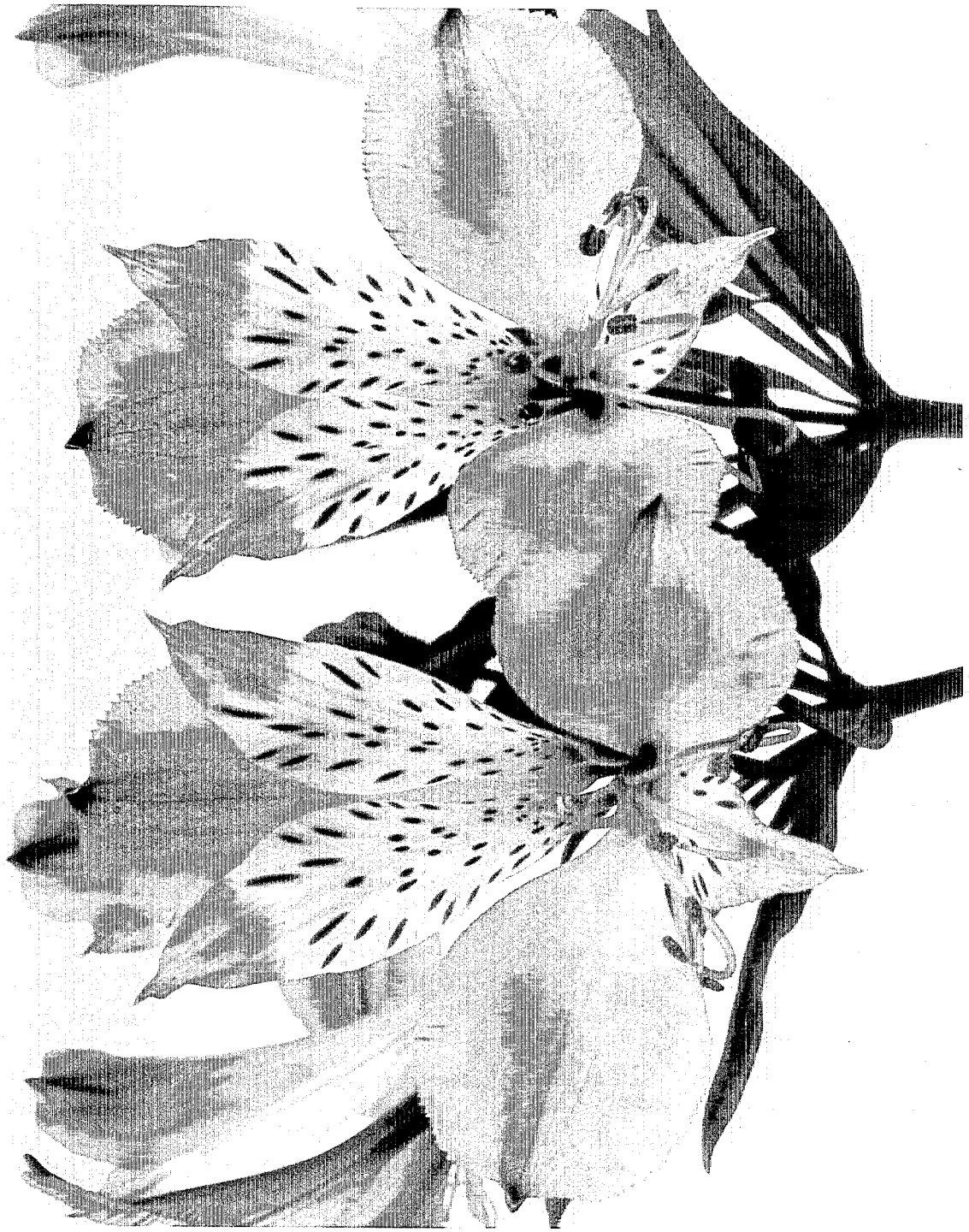

* * * * *